United States Patent [19]

Elfarra

[11] Patent Number: 5,087,441
[45] Date of Patent: Feb. 11, 1992

[54] PROTECTION AGAINST CHEMICALLY-INDUCED KIDNEY DAMAGE BY METHIMAZOLE

[75] Inventor: Adnan A. Elfarra, Madison, Wis.

[73] Assignee: Wisconsin Alumni Research Foundation, Madison, Wis.

[21] Appl. No.: 652,964

[22] Filed: Feb. 8, 1991

Related U.S. Application Data

[62] Division of Ser. No. 454,884, Dec. 22, 1989, Pat. No. 5,010,092.

[51] Int. Cl.$^5$ .................. A61K 49/00; A01N 43/50; A01N 43/52
[52] U.S. Cl. ...................... 424/10; 514/392; 514/395; 514/492
[58] Field of Search ............ 514/392, 395, 492; 424/10

[56] References Cited

PUBLICATIONS

B. Marchant et al., 91 Endo. 747–756 (1972).
T. Zenser et al., 227 J. Pharm. Ex. Ther. 545–550 (1983).
T. Petry et al., 262 J. Bio. Chem. 14112–14118 (1987).
R. Schnellmann et al., 237 J. Pharm. Ex. Ther. 456–461 (1986).
S. Lau et al., 15 Drug Metab. And Disp. 801–807 (1987).
R. Schnellmann, 99 Tox. and App. Pharm. 11–18 (1989).
J. Burchenal et al., 60 Biochimie 961–965 (1978).
J. Filipski et al., 204 Science 181–183 (1979).
J. Yuhas et al., 64 Can. Treat. Rep. 57–64 (1980).
S. Howell et al., 43 Can. Res. 1426–1431 (1983).
C. Kuo et al., 67 Tox. and App. Pharm. 78–88 (1983).
A. Elfarra et al., 33 Biochem. Pharm. 3729–3732 (1984).
A. Elfarra et al., 233 J. Pharm. and Ex. Ther. 512–516 (1985).
L. Ramsammy et al., 34 Biochem. Pharm. 3895–3900 (1985).
P. Williams et al., 237 J. Pharm. and Ex. Ther. 919–925 (1986).
P. Dedon et al., 36 Biochem. Pharm. 1955–1964 (1987).
S. Heyman et al., 82 J. Clin. Invest. 401–412 (1988).
R. Qazi et al., 80 J. Nat. Can. Inst. 1486–1492 (1988).
B. Tune et al., 38 Biochem. Pharm. 795–802 (1989).
J. Cohen et al., 36 Kidney Inter. 730–740 (1989).
L. Ramsammy et al., 238 J. Pharm. Exper. Thero. 83–88 (1986).

Primary Examiner—Leonard Schenkman
Assistant Examiner—T. J. Criares
Attorney, Agent, or Firm—Quarles & Brady

[57] ABSTRACT

Drug treatment therapies and kits for use therewith are disclosed. They involve the use of methimazole and/or its pro-drug carbimazole to reduce nephrotoxic effects of chemical exposure. In one embodiment, a patient receives cisplatin and then is treated with methimazole. The time delay in providing methimazole prevents the methimazole from being substantially expelled by the kidney prior to cisplatin reaching the kidney.

2 Claims, No Drawings

PROTECTION AGAINST CHEMICALLY-INDUCED KIDNEY DAMAGE BY METHIMAZOLE

This invention was made with United States Government support awarded by the National Institutes of Health (NIH), BRSG Grant #RR05912, NIEHS Grant #GM40275, and MARC Grant #RR03182. The United States Government has certain rights in this invention.

This is a division of application U.S. Ser. No. 07/454,884, filed Dec. 22, 1989, issued as U.S. Pat. No. 5,010,092 on Apr. 23, 1991.

This invention relates generally to drugs and other chemicals which cause kidney damage. More specifically, it relates to the use of methimazole in combination with such chemicals to reduce the nephrotoxic effects of such chemicals.

BACKGROUND OF THE INVENTION

Various drugs and other useful chemicals are known to have the side effect of causing renal damage. In the case of drugs, this places undesirable restrictions on the amount of the drug that can be used and the frequency of use, and limits use of the drug to patients who can tolerate the side effects. Even where the short term benefits of using the drug outweigh the problems caused by the side effects, and where the patient is willing to tolerate the side effects, such drugs can adversely affect the patient's long term health. In the case of non-drug chemicals (e.g. work place chemicals, radiation contrast media), nephrotoxic effects can in an analogous manner require exposure to the chemicals to be limited.

There have in the past been various attempts to determine the chemical and biological causes of chemically-induced nephrotoxicity, and attempts to develop means for blocking or reducing these effects. See generally J. Burchenal et al., 60 Biochim. 961–965 (1978); J. Filipski et al., 204 Science 181–183 (1979); J. Yuhas et al., 64 Can. Treat. Rep. 57–64 (1980); S. Howell et al., 43 Can. Res. 1426–1431 (1983); C. Kuo et al., 67 Tox. Ap. Pharm. 78–88 (1983); A. Elfarra et al., 33 Biochem. Pharm. 3729–3732 (1984); A. Elfarra et al., 233 J. Pharm. Ex. Therap. 512–516 (1985); L. Ramsammy et al., 34 Biochem. Pharm. 3895–3900 (1985); P. Williams et al., 237 J. Pharm. Ex. Therap. 919–925 (1986); P. Dedon et al., 36 Biochem. Pharm. 1955–1964 (1987); S. Heyman et al., 82 J. Clin. Invest. 401–412 (1988); R. Qazi et al., 80 J. Natl. Can. Ins. 1486–1488 (1988); B. Tune et al., 38 Biochem. Pharm. 795–802 (1989); A. Berns, *Nephrology Forum*, Kidney International, Vol. 36, pp. 730–740 (1989). The disclosure of these articles and all other articles described herein are incorporated by reference as if fully set forth herein. However, means for reducing nephrotoxicity are typically ineffective, overly expensive, and/or have their own side effects.

In other unrelated work, methimazole (1-methyl-2-mercaptoimidazole) has been used since the early 1940s in connection with thyroid treatment. See generally B. Marchant et al., 91 Endo. 747–756 (1972). It has also been reported that methimazole inhibits prostaglandin H synthase-dependent oxidation. See generally T. Petry et al., 262 J. Biol. Chem. 14112–14118 (1987) and T. Zenser et al., 227 J. Pharm. Ex. Therap. 545–550 (1983).

A few recent reports also describe the effects of methimazole on 2-bromohydroquinone ("BHQ") activity using renal tubules or homogenates. See S. Lau et al., 15 Drug Met. Disp. 801–807 (1987) (BHQ nephrotoxicity may be related to prostaglandin synthesis); R. Schnellmann et al., 237 J. Pharm. Exp. Ther. 456, 459 (1986) (does not protect against BHQ in vitro toxicity); R. Schnellmann, 99 Tox. App. Pharm 11, 12 (1989) (BHQ oxidation probably unrelated to prostaglandin synthesis).

Notwithstanding the over forty years of experience with methimazole, and the many years of attempts to solve nephrotoxicity side effects, a need still exists for improved means for better protecting kidneys against nephrotoxic chemicals.

SUMMARY OF THE INVENTION

One embodiment of the present invention provides a method for treating a mammal. A patient is exposed to both compound A and compound B. Compound A is selected from the group of antibiotics, cisplatin, and S-(1,2-dichlorovinyl)-L-cysteine. Compound B is selected from the group of methimazole and carbimazole. A preferred group of Compound B antibiotics are the aminoglycoside antibiotics (e.g. gentamicin, tobramycin, amikacin, netilmicin, kanamycin, streptomycin, sisomicin, and neomycin). Another group of Compound B preferred antibiotics are the cephalosporin antibiotics (e.g. cephaloridine, cephalothin, cephaloglycin, cepfazolin, cephapirin, cephalexin, cephradine, cefadroxil, cefamandole, cefoxitin, cefaclor, cefuroxime, cefonicid, ceforanide, cefotaxime, moxalactam, ceftizoxime, ceftriaxone, cefoperazone). Other nephrotoxic antibiotics of interest are vancomycin, amphotericin B, and imipenem.

Methimazole may also protect the kidney against nephrotoxicity from cyclosporin and/or contrast media used in radiological studies. For example, contrast media such as sodium diatrizoate, meglumine iothalamate, sodium meglumine diatriazoate, sodium iothalamate, metrizamide, iopamidol, and iohexol are known to have nephrotoxic effects which limit their usefulness. Further, methimazole may protect the kidney from nephrotoxic effects due to chemicals that contain metals (other than just cisplatin), e.g. mercury, lead, chromium, and uranium.

It has been discovered that methimazole will in vivo protect the kidney during exposure to certain compounds even though those compounds do not rely on prostaglandin to cause their toxic effects. Methimazole treatment appears to protect against renal damage by maintaining the integrity of renal cellular membranes and by preventing lipid peroxidative events which aggravate the damage produced by nephrotoxic chemicals.

For some chemicals, the desired protective effect can only be achieved if at least some of the methimazole is provided after the nephrotoxic drug. In this regard, certain drugs (such as cisplatin) take more time than methimazole to reach the kidney in significant amounts. The kidney over time removes methimazole from the body. Thus, if cisplatin is given only after methimazole, the kidney may use up most of the methimazole before the cisplatin reaches the kidney.

In yet another aspect of the invention, kits are provided which include both compound A and compound B. The kits can be in the form of a single injection (or tablet) which contains both compounds, or there can be kits where the compounds are separately packaged.

The objects of the invention therefore include providing methods of treatment and kits of the above kind:

(a) which reduce nephrotoxic affects on the kidney resulting from exposure to certain chemicals;
(b) which permit exposures to higher concentrations of certain drugs and/or more frequent exposures to such drugs; and/or
(c) which permit a wider range of people to use certain drugs.

These and still other objects and advantages of the present invention will be apparent from the description which follows. These embodiments do not represent the full scope of the invention. Rather, the invention may be employed in other embodiments. Reference is therefore made to the claims herein for interpreting the full scope of the invention.

BEST MODES FOR CARRYING OUT THE INVENTION

Materials

Methimazole is available as an anti-thyroid drug marketed by Eli Lilly. It is typically given to humans orally in tablet form, with dosages of 5 - 50 mg per tablet. It is also available in its chemical form from Aldrich. A prodrug form of methimazole, known as carbimazole (neomercazole), is also widely available (e.g. in Great Britain) and has the following formula:

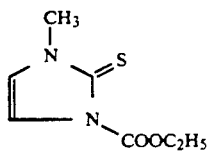

It breaks down in mamalian plasma to give methimazole.

Experimental Design

Young male adults Sprague-Dawley rats (200–300 g) were housed individually in metabolism cages that allowed the separation of urine and feces. A 12-hour light cycle was maintained and water and feed were provided ad libitum. Nephrotoxicity was assessed by performing one or more of the following renal function tests. One test was a blood urea nitrogen concentration test, an indicator of renal glomerular filtration rates. Another test was determining urinary glucose excretion rates, an indicator of tubular reabsorption rates. A third test was histopathological examination of renal tissues. A fourth test is a determination of glutathione and glutathione ratio as an indication of lipid peroxidation processes.

Antibiotics

Rats were given a single dose of the antibiotic cephaloridine (1,000 mg/kg i.p.) dissolved in alkaline saline. Control rats were given alkaline saline alone. Some non-control rats had been pre-treated thirty minutes before by being given a single dose of methimazole (20 mg/kg i.p.) in saline. Rats were killed 24 hours after cephaloridine treatment. Rats treated with cephaloridine (but not methimazole) exhibited the expected nephrotoxic effects. Animals pretreated with methimazole were significantly protected against the nephrotoxic effects of this antibiotic.

Metals

Rats were given a single dose of cisplatin (5 mg/kg i.p.) in saline (or were given saline alone for controls). Some rats were given a single dose of methimazole (20 mg/kg i.p.) 30 minutes prior to cisplatin treatment, others were given that dose 30 minutes after cisplatin treatment, and still others were given no methimazole. All rats were killed five days after the cisplatin treatment. Nephrotoxicity was assessed. The experiment shows that giving methimazole before cisplatin did not protect, but that giving methimazole 30 minutes after cisplatin provided significant protection. Thus, for cisplatin (and other chemicals that are slow to reach the kidney), exposure to methimazole may have to be delayed and/or repeated.

S-(1,2 dichlorovinyl)-L-cysteine ("DCVC")

Rats were given a single dose (100 mg/kg i.p.) of DCVC dissolved in alkaline saline. DCVC is a nephrotoxic metabolite of tri-chloroethylene, an environmental toxin present in some work places and present in some drinking water supplies. Again controls were given saline alone. Some rats were pretreated with a single dose of methimazole (20 mg/kg i.p.) and then killed 24 hours after DCVC treatment. Other tests were run with dosages lower than 20 mg/kg. It was determined that dosages lower than 20 mg/kg did not protect the rats significantly against DCVC, whereas the higher dosages did.

Repeated Exposure

The effect of repeated exposure is now being studied. In particular, protection against a nephrotoxic aminoglycoside antibiotic, gentamicin, is being studied. Rats have been given daily injections of gentamicin (200 mg/kg i.p.) for 5 days, with daily injections of methimazole being given (20 mg/kg i.p.) 30 minutes after gentamicin is given. It is expected that nephrotoxic effects will be reduced, notwithstanding repeated exposures.

General Comments

The particular nephrotoxic chemical to which a human or other animal is to be exposed can have its methimazole or carbimazole dosages and preferred exposure patterns established by techniques analogous to those above. After conducting rat and/or ape experiments, one can give humans varying dosages up to levels that have already been approved for human use.

It will be appreciated that the above describes only the preferred embodiments of the invention. A number of other modifications and changes are intended to be within the scope of the invention. For example, other prodrugs that in vivo generate methimazole are also intended to be covered. Thus, the invention is not to be limited to the preferred embodiments above.

I claim:

1. A method for reducing the nephrotoxicity of cisplatin that is being administered to a live mammal in need thereof, the method comprising:
   administering to the live mammal the ciplatin as well as an effective amount of a compound selected from the group of methimazole and carbimazole so as to reduce the nephrotoxicity of the cisplatin.

2. The method of claim 1, wherein the compound is methimazole and at least some of the administering of methimazole occurs after the administration of cisplatin to the mammal.

* * * * *